United States Patent [19]

Francese et al.

[11] 4,182,875

[45] Jan. 8, 1980

[54] PRODUCTION OF CHLORO-BIS(ALKYLAMINO)-S-TRIAZINES

[75] Inventors: Renato Francese; Roberto Esposito, both of Turin, Italy

[73] Assignee: Rumianca S.p.A., Turin, Italy

[21] Appl. No.: 953,319

[22] Filed: Oct. 20, 1978

[30] Foreign Application Priority Data

Oct. 20, 1977 [IT] Italy .............................. 28810 A/77

[51] Int. Cl.² .......................................... C07D 251/50
[52] U.S. Cl. ................................................... 544/204
[58] Field of Search ......................................... 544/204

[56] References Cited

U.S. PATENT DOCUMENTS 3,681,337  8/1972  Petree .................................. 544/204

*Primary Examiner*—John M. Ford
*Attorney, Agent, or Firm*—Sughrue, Rothwell, Mion, Zinn and Macpeak

[57] ABSTRACT

In the commercial process for preparing chloro-bis(aklylamino)-s-triazines by step-wise replacement of two chlorine atoms of cyanuric chloride with alkylamino groups in which a molar excess of alkylamine is used in the second replacement step, the formation of tris-(alkylamino)-s-triazines is suppressed by submitting the reaction mixture, after the second replacement step is completed, to a pressure not exceeding 400 mm Hg, at a temperature not exceeding about 55° C. and for a period not exceeding about 15 minutes, thereby removing the excess alkylamine from said reaction mixture by volatilization without substantially removing the other components of the reaction mixture.

7 Claims, No Drawings

PRODUCTION OF CHLORO-BIS(ALKYLAMINO)-S-TRIAZINES

The present invention relates to the preparation of chloro-bis(alkylamino)-s-triazines by means of a process which allows the elimination, or at least the substantial reduction, of the formation of tris(alkylamino)-s-triazines.

The chloro-bis(alkylamino)-s-triazines are compounds definable by means of the general formula

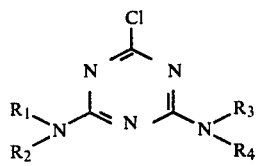

where $R_1$, $R_2$, $R_3$ and $R_4$ independently are hydrogen, an alkyl radical containing from 1 to 5 atoms of carbon, or particular groups of a different nature from the alkyl group.

The chloro-bis(alkylamino)-s-triazines are valued herbicides and the compounds most known belonging to this group are: 2-chloro-4-ethylamino-6-isopropylamino-s-triazine (atrazine), 2-chloro-4,6-bis(ethylamino)-s-triazine(simazine) and 2-chloro-4,6-bis(isopropylamino)-s-triazine (propazine). The herbicidal characteristics of these compounds are described in U.S. Pat. No. 2,891,855 here given as a reference.

The chloro-bis(alkylamino)-s-triazines are generally prepared from cyanuric chloride by successive substitution of two atoms of chlorine, as reported, for example, by W. Pearlman and C. K. Banks in J. Am. Chem. Soc. 70, 3726 (1948). In practice the reaction is carried out according to the general scheme:

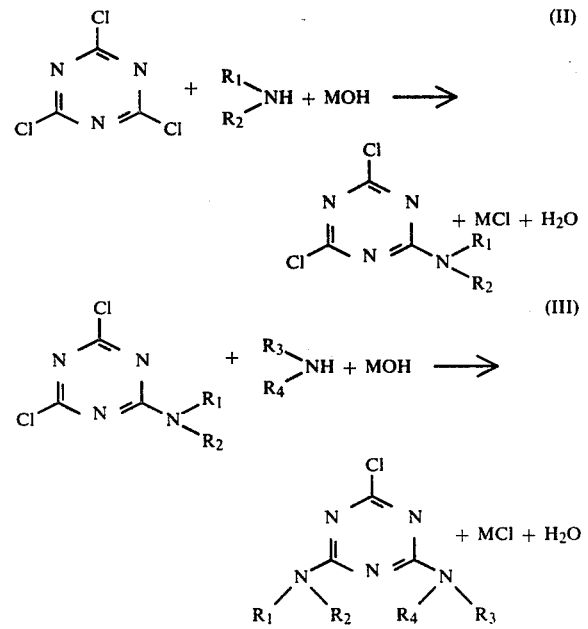

where M represents an alkali metal.

In particular the preparation of atrazine is generally carried out by a discontinuous method, by reacting, in a first reaction stage, cyanuric chloride with isopropylamine in the presence of sodium hydroxide to give 2,4-dichloro-6-isopropylamino-s-triazine. This latter is reacted, in a second stage, with ethylamine and with a further quantity of sodium hydroxide with the subsequent formation of the desired product: 2-chloro-4-ethylamino-6-isopropylamino-s-triazine.

The reactions described may be carried out in an aqueous medium or in an organic medium. Generally it is preferred to conduct the reactions in a water-organic compound medium, using as organic compound a solvent for cyanuric chloride which is insoluble in water, or is partially or totally soluble in the same, and thus a two-phase or single-phase water-organic compound medium.

Generally the reaction (II) given above is carried out by using stoichiometric quantities of the reagents, while the reaction (III) is carried out with a quantity of alkylamine and of sodium hydroxide greater than those needed for the production of chloro-bis(alkylamino)-s-triazine. This method of operation is justified by the need to eliminate the 2,4-dichloro-6-alkylamino-s-triazine completely from the reaction medium in view of the undesirable characteristics of such compounds. Thus, for example, 2,4-dichloro-6-isopropylamino-s-triazine has skin-irritant properties to such an extent that it must not be present in the final product in quantities greater than about 0.5% by weight.

On the other hand the use of excess alkylamine results in disadvantages due to the formation of tris(alkylamino)-s-triazine, by reaction of the excess alkylamine with the chloro-bis (alkylamino)-s-triazine. For example, the reaction of ethylamine with 2-chloro-4-ethylamino-6-isopropylamino-s-triazine results in the formation of 2,4-bis(ethylamino)-6-isopropylamino-s-triazine. This latter compound is undesirable in that it renders the recovery of atrazine from the reaction products difficult, hinders the grinding of the dried atrazine and reduces the stability and flowability of the liquid formulations containing atrazine. Probably these undesirable effects are caused, at least in part, by the 2,4-bis-(ethylamino)-6-isopropylamino-s-triazine, which is a tacky solid of low melting point and waxy appearance. This by-product forms in the stage of recovery of the reaction products, especially in the stage of distillation of the organic solvent used in the reaction medium, rather than during the reaction (III) described above.

Therefore various expedients have been proposed in the art to separate, or at least to render to some extent nonactive, the unreacted alkylamine at the end of the reaction (III) and in particular to separate, or to deactivate, the ethylamine in the case of the preparation of atrazine.

Thus, for example, according to U.S. Pat. No. 3,681,335 on completion of the formation of the chloro-bis(alkylamino)-s-triazine, a strong acid is added to the reaction medium to bring the pH from 11.5–12 to values of the order of 5–9 (preferably of the order of 6.5–7.5). In this manner the alkylamine is deactivated and the distillation of the organic solvent may be carried out without danger of formation of tris(alkylamino)-s-triazine. According to the patent under discussion, the pH is brought back to values of the order of 11–12.5 in the residual suspension from the distillation containing the chloro-bis(alkylamino)-s-triazine before the separation of the latter is carried out by means of filtration. The characteristics of filterability are thus improved.

Moreover, according to U.S. Pat. No. 3,681,337, immediately after the end of reaction (III), cyanuric chloride is added to the reaction mixture in such amounts as to neutralize the free amine and form the dichloro-alkylamino-s-triazine, which is then hydrolized together with the free cyanuric chloride. Since the hydrolysis products are soluble in water their removal becomes easy.

Finally, according to U.S. Pat. No. 3,705,156 formaldehyde is added to the products of the reaction (III), in order to induce the formation of condensation products between the formaldehyde and the free alkylamine. These condensation products are removed during the distillation and the subsequent filtration.

The known processes, by achieving only the object of avoiding, or at least minimising the formation of the tris (alkylamino)-s-triazine have disadvantages essentially resulting from the addition of further substances to the reaction mixture, with consequent formation of new chemical species. Such a method of operation may result in disadvantages relative to the purity of the final desired product. Moreover the said processes are burdensome due to the number of treatments required.

The object of the present invention is to overcome these disadvantages and to prepare chloro-bis(alkylamino)-s-triazines free, or substantially free, of tris-(alkylamino)-s-triazine.

The invention provides a method of suppressing the formation of tris(alkylamino)-s-triazines in a process for preparing chloro-bis(alkylamino)-s-triazines by means of the step-wise replacement of two chlorine atoms of cyanuric chloride with alkylamino groups in an alkaline medium comprising a mixture of water and an organic compound which is a solvent for cyanuric chloride, and in which a molar excess of alkylamine is used in the second replacement step, which comprises submitting the reaction mixture, after the second chlorine atom has been replaced with an alkylamino group, to a pressure not exceeding about 400 mm Hg, at a temperature not exceeding about 55° C. and for a period not exceeding about 15 minutes, thereby removing the excess alkylamine from said reaction mixture by volatilization without substantially removing said organic compound and the other components of the reaction mixture. The removal of the organic compound from the reaction mixture and the recovery of the chloro-bis(alkylamino)-s-triazine are the carried out by conventional methods.

The excess alkylamine used in the substitution of the second chlorine atom of cyanuric chloride is generally not greater than 15% molar, values of from 1 to 5% and preferably of the order of 3% being conveniently used. With such excesses it is in fact possible to convert the 2,4-dichloro-6-alkylamino-s-triazine completely, or substantially completely.

The present invention is based essentially on the finding that the volatilization of the said excess alkylamine occurs without substantial formation of tris (alkylamino)-s-triazine, when submitting the reaction mixture, once the replacement of the second atom of chlorine of cyanuric chloride is completed, to a subatmospheric pressure possibly with the assistance of a flow of inert gas, without removing substantial quantities of organic solvent or other constituents of the reaction medium.

The operating conditions used for the removal of the alkylamine depend on the nature of the alkylamine which must be volatilized.

Generally speaking, said removal is carried out at pressures not exceeding about 400 mmHg and at temperatures not exceeding 55° C., nitrogen or other inert gas possibly being passed through the reaction mixture.

Conveniently, the removal of the excess alkylamine is carried out immediately after the end of the replacement step of the second chlorine atom of cyanuric chloride, or at least within a time not greater than about 10-15 minutes. In the case in which it is not wished to proceed immediately with the said removal is is suitable to cool the reaction mixture to a range of temperatures in which further substantial transformations do not occur.

The said volatilization is carried out in a time not greater than about 15 minutes and preferably not greater than about 10 minutes. The said times are the maximum within which the reaction mixture is maintained under conditions of volatilization of the alkylamine. Finally, the removal of the alkylamine should be carried out without substantial removal of the organic solvent or the other constituents of the reaction mixture. Generally, less than 5% of the organic solvent and negligible quantities of water are removed together with the excess alkylamine.

The reaction mixture thus treated may be subjected to distillation of the organic solvent and to recovery of the chloro-bis(alkylamino)-s-triazine, thus obtaining a product free from tris(alkylamino)-s-triazine, or at least having a content of the latter less than about 0.05% by weight. Therefore the removal of the excess alkylamine from the reaction mixture, provided that it is carried out in the manner indicated, has been shown to be an extremely efficient method for obtaining chloro-di(alkylamino)-s-triazines with a zero, or negligibly low, content of tris(alkylamino)-s-triazine. Moreover the said process is simple and economical.

The chloro-bis(alkylamino)-s-triazines obtained according to the present invention are useful in herbicidal formulations (both as wettable powder and as liquid suspensions) which are characterised by a great facility of use and by an increased herbicidal efficiency. These formulations do not have any disadvantages resulting from tris(alkymalino)-s-triazines in their storage or their use.

By means of the process of the present invention there may be prepared all the compounds definable by means of the general formula (I), in which $R_1$, $R_2$, $R_3$ and $R_4$ independently are hydrogen, alkyl radicals either the same of different, having from 1 to 5 atoms of carbon, or other particular groups different from alkyl groups. Examples of alkyl radicals are: methyl, ethyl, isopropyl, cyclopropyl, n-butyl, sec-butyl and tert-butyl.

In the description which follows, specific reference will be made to the preparation of 2-chloro-4-ethylamino-6-isopropylamino-s-triazine. This is for reasons of simplicity, it being taken into account that wholly similar considerations are valid for the other chloro-bis(alkylamino)-s-triazines.

(a) Preparation of
2,4-dichloro-6-isopropylamino-s-triazine

In stage (a) cyanuric chloride, isopropylamine and sodium hydroxide are reacted to produce 2,4-dichloro-6-isopropylamino-s-triazine according to the following scheme

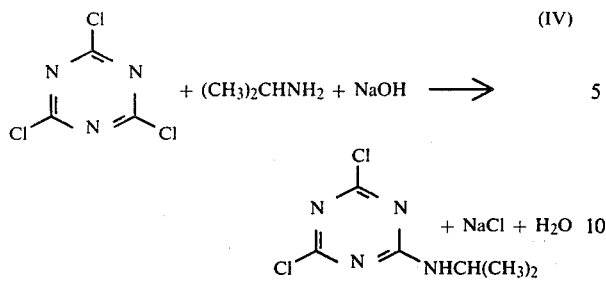

(IV)

+ NaCl + H₂O

The quantities of isopropylamine and of sodium hydroxyde are equivalent, or nearly equivalent, to those needed for the formation of the 2,4-dichloro-6-isopropylamino-s-triazine. In place of sodium hydroxide there may be used sodium carbonate, or the hydroxide or carbonate of other alkali metals, such as lithium and potassium.

The reaction is carried out in the presence of an organic compound, inert under the reaction conditions and having a good solvating power towards cyanuric chloride. Organic solvents suitable for the purpose are: diethyl ether, dioxan, diethyl Cellosolve, benzene, toluene, xylene, chlorobenzene, acetone, methyl ethyl ketone, carbon tetrachloride or such other organic solvents known in the art in respect of the preparation of chloro-di(alkylamino)-s-triazines. There solvents are preferably used in mixture with water, in the form of a single-phase system, such as water-acetone and water-dioxan, or a two-phase system, such as water-benzene and water-chlorobenzene. As a rule the cyanuric chloride is fed in the form of a solution in the chosen organic solvent, while the inorganic base and the alkylamine are fed in in the form of an aqueous solution. In the choice of the solvent it is also necessary to take account of its separability, for example, by means of distillation, from the 2-chloro-4-ethylamino-6-isopropylamino-s-triazine finally produced. The quantities of organic solvent and of water used are not particularly critical; it is however, convenient to maintain the weight ratios between the two at values of from 3:1 to 3:2. Moreover good results are obtained by regulating the feeds such that the concentration of the 2,4-dichloro-6-isopropylamino-s-triazine at the end of stage (a) is from 10 to 20% by weight with respect to the weight of the chosen organic solvent.

The temperature is generally kept at a value of from −5° to 60° C. Overpressure is not generally applied, or the overpressure necessary to maintain the reaction medium in the liquid phase is applied.

The 2,4-dichloro-6-isopropylamino-s-triazine may be prepared by a continuous or a discontinuous process. In the second case the sodium hydroxide and the isopropylamine are generally added in the form of aqueous solutions to the cyanuric chloride dissolved in the chosen organic solvent.

At the end of stage (a) it is possible to carry out a separation of materials from the reaction mixture, such as the aqueous phase, or the reaction mixture may be conveyed directly to the following reaction stage.

(b) Preparation of
2-chloro-4-ethylamino-6-isopropylamino-s-triazine

In stage (b) the 2,4-dichloro-6-isopropylamino-s-triazine obtained in stage (a), ethylamine and sodium hydroxide are reacted to produce 2-chloro-4-ethylamino-6-isopropylamino-s-triazine according to the scheme:

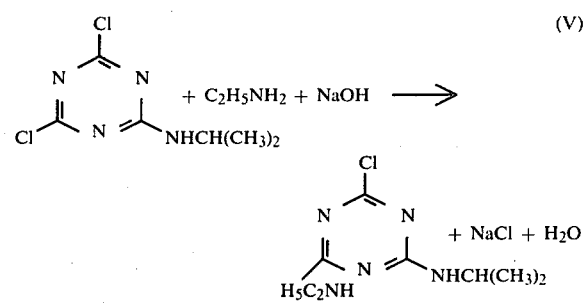

(V)

+ NaCl + H₂O

The ethylamine and sodium hydroxide are generally used in a molar excess of from 1 to 5% with respect to the stoichiometric value. Usually this excess is maintained at values of the order of 3%. The ethylamine and the sodium hydroxide are conveniently fed in in the form of an aqueous solution.

The reaction is conveniently carried out at a temperature of from 25° to 90° C. and for a period such as to completely convert the 2,4-dichloro-6-isopropylamino-s-triazine, or at least to convert more than about 99.5% of this compound.

The other operating conditions for stage (b) are entirely similar to those described for stage (a).

(c) Removal of the ethylamine and separation of the reaction products.

The ethylamine is evaporated from the reaction mixture obtained in stage (b) according to the procedure already described.

In the case of a discontinuous process, the removal of the ethylamine may be carried out in the reactor used for the substitution of the second chlorine atom of cyanuric chloride. In this case the reactor may be connected directly to a vacuum source. Alternatively the reaction mixture is transferred to a distillation column in which the ethylamine is first volatilised and the organic solvent is thereafter recovered. In the case of a continuous operation, the reaction mixture passes continuously firstly into apparatus in which the ethylamine is volatilised and then to further apparatus suitable for the recovery of the solvent.

In particular in the case of the production of 2-chloro-4-ethylamino-6-isopropylamino-s-triazine, in a water-organic compound (water-toluene) medium, with a molar excess of 1–6% of ethylamine with respect to the stoichiometric value, the removal of the latter is conveniently carried out at a pressure of the order of 100 mmHg, at a temperature of about 50°–55° C. and for periods not exceeding about 10 minutes.

At the end of the treatment described the distillation of the organic solvent is carried out. The residue from the distillation consists of a dense suspension of 2-chloro-4-ethylamino-6-isopropylamino-s-triazine, which is subjected to filtration and to recovery of the atrazine according to the known art. This atrazine, and the other compounds of general formula (I) thus prepared, contain less than about 0.05% by weight of tris-(alkylamino)-s-triazine.

EXAMPLE 1

A reactor of 20 liter capacity, provided with an agitator, a thermometer and two separate apertures for the feed of the reagents, is used. The reactor is furnished with means for its cooling. Into the reactor are loaded initially a solution of about 1840 g (10 moles) of cyanuric chloride in about 5000 g of toluene (boiling point 110.6° C.). Hardly has the temperature of the solution stabilised at 5° C. than there are simultaneously added, under strong agitation, 840 g (10 moles) of an aqueous solution containing 70% by weight of isopropylamine and 1340 g (10 moles) of an aqueous solution containing 30% by weight of sodium hydroxide.

The two feed rates are controlled so that the addition of the isopropylamine solution finishes in 25 minutes and that of the sodium hydroxide in 28 minutes.

During the addition, the temperature rises from 5° C. up to 20°-22° C., while the pH, from an initial value of 2-3, rises to a maximum value of 9.5 then to fall to 6-7.

After the addition, the mixture is maintained for 10 minutes at 20° C., 2000 g of dilute hydrochloric acid (0.1% by weight) are introduced so as to bring the pH of the medium to a value of about 2-3. The mixture is agitated for 15 minutes and then decanted and the aqueous layer is separated.

To the solution of 2,4-dichloro-6-isopropylamino-s-triazine in toluene remaining in the reactor are added, under strong agitation, about 915 g of an aqueous solution containing 50% by weight of ethylamine (10.15% moles) and about 1353 g of an aqueous solution containing 30% by weight of sodium hydroxide (10.15 moles). The said solutions are added in the same manner as in the first reaction step. During the second addition the temperature rises from 25° to 50° C. and the final pH is equal to 11.5-12. The suspension thus obtained is divided into two parts as quickly as possible. One part (A) is immediately subjected to distillation at atmospheric pressure and at a temperature of 85° C., to distill of the organic solvent. From the distillation residue is separated the 2-chloro-4-ethylamino-6-isopropylamino-s-triazine, which is washed and dried. The other part (B) is subjected to evaporation at a pressure of 100 mmHg and at a temperature equal to about 50° C. for a time of 10 minutes. For this purpose the receptacle containing the part (B) of the mixture is connected to an ordinary vacuum pump, furnished with a vacuum-meter and a pressure regulating valve.

As well as the ethylamine there is thus removed 1-2% of the organic solvent, present in the suspension, together with a negligible quantity of water.

The residue from the evaporation is then stored at 50° C. for 20 hours. After this period of time, the solvent contained in sample (B) is distilled off at atmospheric pressure and at a temperature of 85° C. From the distillation residue is separated the 2-chloro-4-ethylamino-6-isopropylamino-s-triazine, which is subjected to washing and drying.

The quantity of 2,4-di(ethylamino)-6-isopropylamino-s-triazine with respect to the atrazine is determined. The results are given in Table 1.

EXAMPLES 2 AND 3

These runs are carried out as in Example 1, the ethylamine being used in a molar excess of 3% and 6% respectively. The results are given in Table 1.

Table 1

| Example | Sample | % molar excess $EtNH_2$ | $TAT^+$ % dry weight |
|---------|--------|-------------------------|---------------------|
| 1 | A | 1.5 | 0.9 |
|   | B | 1.5 | $NM^{++}$ |
| 2 | A | 3.0 | 1.7 |
|   | B | 3.0 | $NM^{++}$ |
| 3 | A | 6.0 | 3.2 |
|   | B | 6.0 | $NM^{++}$ |

$^+$ TAT = 2,4-di(ethylamino)-6-isopropylamino-s-triazine.
$^{++}$ NM = not measurable (less than 0.05% by weight).

We claim:

1. In a process for preparing chloro-bis(alkylamino)-s-triazines by means of the step-wise replacement of two chlorine atoms of cyanuric chloride with alkylamino groups in an alkaline medium comprising a mixture of water and an organic compound which is a solvent for cyanuric chloride and in which a molar excess of alkylamine is used in the second replacement step, the method of suppressing the formation of tris(alkylamino)-s-triazines which comprises submitting the reaction mixture, after the second chlorine atom has been replaced with an alkylamine group, to a pressure not exceeding about 400 mm Hg, at a temperature not exceeding about 55° C. and for a period not exceeding about 15 minutes, thereby removing the excess alkylamine from said reaction mixture by volatilization without substantially removing said organic compound and the other components of the reaction mixture.

2. The process of claim 1, wherein an inert gas is passed through the reaction mixture during the volatilization treatment.

3. The process of claim 1, wherein said molar excess of alkylamine does not exceed 15%.

4. The process of claim 1, wherein said molar excess of alkylamine is from 1 to 5%.

5. The process of claim 1, wherein said period does not exceed about 10 minutes.

6. The process of claim 1, wherein chloro-bis(alkylamino)-s-triazine containing less than about 0.05% by weight of tris(alkylamino)-s-triazine is produced.

7. The process of claim 1, wherein 2-chloro-4-ethylamino-6-isopropylamino-s-triazine is produced with a 2,4-bis (ethylamino)-6-isopropylamino-s-triazine content of less than 0.05% by weight.

* * * * *